United States Patent
Young

[11] Patent Number: 6,004,283
[45] Date of Patent: Dec. 21, 1999

[54] HINGE WITH LOCKING MEANS

[75] Inventor: David Ernest Young, Watlington, United Kingdom

[73] Assignee: Johnson & Johnson Professional, Inc., Ravnham, Mass.

[21] Appl. No.: 08/931,681

[22] Filed: Sep. 16, 1997

[30] Foreign Application Priority Data

Sep. 25, 1996 [GB] United Kingdom .................. 9619968

[51] Int. Cl.$^6$ ...................................................... A61F 5/00
[52] U.S. Cl. .............................................. 602/16; 602/26
[58] Field of Search ......................................... 602/16, 26

[56] References Cited

U.S. PATENT DOCUMENTS

| | | | |
|---|---|---|---|
| 4,738,252 | 4/1988 | Friddle et al. | 602/16 |
| 4,817,588 | 4/1989 | Bledsoe | 602/16 |
| 5,407,420 | 4/1995 | Bastyr et al. | 602/16 X |
| 5,611,773 | 3/1997 | Nash et al. | 602/16 |
| 5,630,791 | 5/1997 | Glynn | 602/16 |

*Primary Examiner*—Jerome W. Donnelly
*Assistant Examiner*—Denise Pothier
*Attorney, Agent, or Firm*—Michael Q. Tatlow

[57] ABSTRACT

A uniaxial orthopaedic hinge (1000, 2000) has a substantially circular body forming a recessed housing (1022, 2022). A back plate (1006, 2006) has an extension into a stub arm (1004, 2004) for attaching to the arm of an orthosis and is fixed to the recessed housing (1022, 2022). A locking plate (1008, 2008) also has an extension into a stub arm (1002, 2002) and is disposed in a parallel manner between the recessed housing (1022, 2022) and the back plate (1006, 2006). The circular recessed housing (1022, 2022) is provided with a recess (1100, 2100) housing a lock actuator (1102, 2102) having a latching dog (1126, 2126) and also fitted with a biasing leaf spring (1104, 2104). The latching dog (1126, 2126) co-operates with a latching hole (1128, 2128) in the locking plate (1008, 2008) when the hinge (1000, 2000) is in the fully extended position. A lifting cam (1110, 2110) underlies the lock actuator (1102, 2102) and has a cam lifting lever which extends through the face of the circular recessed housing (1022, 2022). The cam lifting lever is moved through about 90° to release the latching dog (1126, 2126) so that the hinge (1000, 2000) may move with free or controlled motion. When the cam lifting lever is switched to the "on" position, the latching dog (1126, 2126) is brought into contact with the locking plate (1008, 2008) under the influence of the spring (1104, 2104). The hinge (1000, 2000) moves freely unless it is fully extended, at which point the latching dog (1126, 2126) once again engages the locking plate (1008, 2008), locking the hinge mechanism (1000, 2000) in full extension.

5 Claims, 6 Drawing Sheets

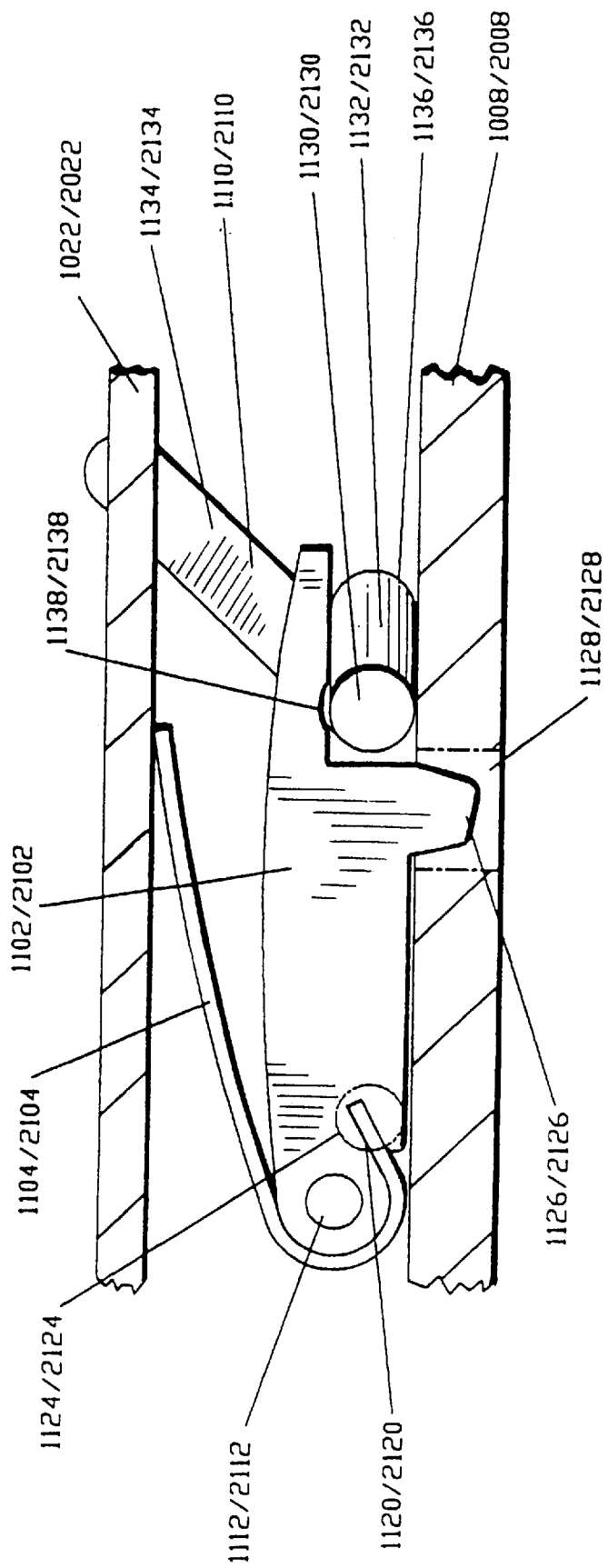

HINGE WITH LOCKING MEANS

This invention relates to a hinge with locking means for use in orthoses, orthopaedic splints and braces employed at the knee.

Mechanically, the knee is a modified, crossed, four bar linkage comprising the rigid elements femur, tibia and the anterior and the posterior cruciate ligaments. Its axis of rotation moves backwards or posteriorly as the knee is flexed from the fully extended position. The locus or track of the axis of knee rotation is called the "Instant Centre Pathway" which exactly defines the moving path of the centre of knee rotation at any given instant.

In a first, very widely used type, there are two hinge arms each having its own pivot and also each having a set of gear teeth about the periphery of that part which extends between the pivots. The arms are so sized and arranged that the gear teeth mesh between the pivot points, thereby integrating the arm movements. Thus if one arm moves, the other must move as well. This type is generally referred to by those skilled in the art as the geared bi-axial, geared duocentric or geared polycentric type. The latter term is perhaps the most widely recognised. This type of hinge is not at all physiological in the way it moves and its mechanical action is quite unlike that of the human knee. Consequently such a hinge cannot accommodate or track the complex motion of the knee properly.

Another type of hinge design used in orthopaedic splints and braces employed at the knee has two hinge arms, each having its own pivot but in this design there are no gear teeth. Thus, in this type, the arm movements are not integrated and each arm can always move independently without affecting the other. This type of hinge is generally referred to by those skilled in the art as the true bi-axial, true bi-pivotal or simply just bi-pivotal type. It continues to grow in popularity with the realisation that such a construction is superior to the others in providing the freedom necessary to accommodate the complex and changing locus of the axis of the knee throughout the entire flexion/extension cycle.

However, a third type, only slightly less popular than the geared polycentric type, has two hinge arms which are joined at and flex about a single pivot. This type is generally referred to by those skilled in the art as the uni-axial, uni-pivotal or monocentric type. Like the geared polycentric hinge, this type is not physiological but because it can be made simply and cheaply, basic designs have frequently found favour in braces and orthoses used in the early phases of treatment and rehabilitation following injury to or surgery on the knee, such as rupture and repair of the anterior cruciate ligament. Most users and manufacturers are aware that uniaxial hinges offer little in the way of physiological tracking or accommodation of natural knee motion. However, the argument made by both groups in favour of using uniaxial hinge usually relates to cost and also propounds that in the acute situations, where most use of this type occurs, ranges of motion are small and activity levels are low.

Recently there has been an upsurge of interest amongst orthopaedic surgeons in uniaxial rehabilitative knee braces which can provide not only the usual restriction of extension and flexion movement which is required at the injured or repaired knee but which will, in addition, optionally lock in full extension as the wearer achieves this position, say, upon standing up from a seated position. This action is particularly desirable in a patient who is or who is thought likely to be less than fully compliant with a prescribed rehabilitative regime in which exercises involving full extension are called for. The underlying reason is that in an anterior cruciate ligament repair, the surgeon will have demonstrated to his own satisfaction that the knee can be fully extended before he completes the procedure. In order that the patient will continue to have a full range of motion at the knee, the surgeon will call for the rehabilitation regime to encourage the patient to fully extend the knee. However, the latter, either because of pain, stiffness or laziness, may fail to do so and consequently not be able to fully extend the knee. Some such patients will blame the surgeon for a sub-optimal result and hence there is an incentive to seek to prescribe devices which will at least partially overcome non-compliance in the patient.

The origin of single pivot hinges in general is lost in the mists of time but it is found in pre-historic flails used for grain and in early jewellery. The uniaxial hinge has been used in a basic form since the earliest days of the orthotic profession and this probably emerged from its widespread earlier use by makers of military armour.

In 1855, H. H. Smith writing in the American Journal of Medical Science described a true splint but which he called an artificial limb which featured a uniaxial hinge at the knee. It does not appear to have had any means for controlling flexion or extension. In 1866, U.S. Pat. No. 58,403 to R. J. P. Goodwin, described a splint primarily for fractures which had a uniaxial hinge and a slot and screw arrangement for compressively locking the arms of the splint in a selected position in what is effectively a continuously variable manner.

Mechanisms which will automatically lock a uniaxial hinge in a knee brace or orthosis at full extension have been known for many years and were most actively developed around patients who suffered the musculoskeletal sequelae of poliomyelitis and those with other deformities of the lower limb. U.S. Pat. No. 2,433,570 to Markkula in 1947, disclosed a leg brace knee lock in which the lower hinge arm is provided with an arcuate notch which faces upwards at full extension and is engaged by a corresponding arcuate cam on a locking lever secured in a bifurcated saddle extension of the upper hinge arm. A biasing spring in the form of an elastic band connected the locking lever to another member on the lower part of the brace. This arrangement tends to encourage locking as the patient stands up and this condition is maintained until the patient lifts the locking lever to disengage the lock to allow flexion when sitting down is required.

This type of arrangement has subsequently become known as a "bale lock" where the locking lever extends between both lateral and medial hinges to form a bale arm behind the knee. The provision of a notch in the end of a first hinge arm and a corresponding locking extension to a locking lever mounted on a second hinge arm has become known as a detent mechanism, which as the name implies, provides for ease of release from a locked position of components under load.

A brief but clear disclosure of this type of locking mechanism is given in U.S. Pat. No. 5,188,584 to Petrofsky et al, in respect of a uniaxial hip hinge.

Non-orthopaedic developments of this type of hinge locking mechanism which provide for a plurality of positions and functions were described in U.S. Pat. Nos. 2,911,245 and 3,352,580, both to Kurz, in which a ratchet and pawl arrangement is employed.

In U.S. Pat. No. 3,826,251 to Ross there was disclosed another detent automatic locking mechanism in which a detent pin is biased towards the locking position when the brace is weight bearing and away from the locked position when the load is taken off the brace, this latter action is assisted by a biasing "off" spring. This mechanism depends, of course, for its action upon being used in a weight bearing orthosis whereas in rehabilitation braces this is almost never the case. Similarly, U.S. Pat. No. 4,456,003 to Allard et al describes a biased detent mechanism for a weight bearing brace, though in this case the bias is "on".

In a commercial catalogue and price list of Otto Bock Orthopadische Industrie Kg, 3428, Duderstadt, Germany for 1976 there are illustrated numerous variants of the automatic locking detent type mechanism for uniaxial knee and hip hinges. This company is known to have been operating from Minneapolis in the USA from at least 1982 with a number of these items on sale to the orthotic profession.

An interesting disclosure is made in U.S. Pat. No. 4,520,804 to Di George where separate ratchet and pawl mechanisms are provides for extension and flexion, respectively, in a uniaxial hinge. Both pawls may be fully disengaged to allow free movement in the direction which they control.

U.S. Pat. No. 5,409,449 to Nebolon discloses a uniaxial hinge mechanism for an orthopaedic knee brace which combines the provision of discontinuous means for limiting flexion and extension and a detent mechanism for automatically locking the hinge in full extension. The means for limiting flexion and extension appear to correspond with the disclosures of Rolfe op cit. The detent mechanism bears striking structural and functional similarities to several other detent mechanisms, particularly those illustrated in U.S. Pat. No. 2,433,570 to Markkula, in the commercial literature of Otto Bock from 1976 and in U.S. Pat. No. 5,188,584 to Petrofsky et al, in op cit.

With a single exception, all the mechanisms for causing a uniaxial orthopaedic hinge to lock automatically in full extension, which have been located, involve structures where a recessed or cutaway portion on the outside edge of a first hinge arm is engaged by a dog or detent element mounted on a second hinge arm, in most cases acting under the influence of a biasing spring, mounted substantially in the same plane as the hinge arms.

The exception is the well known ring-lock or drop-lock hinge where, at full extension, a metal encircling element, disposed about a first upper hinge arm, descends under gravity to encircle an extension from or the pivotal portion of the body of a second hinge arm, thus jamming the hinge and so preventing motion of it.

According to the present invention there is provided a hinge for use in an orthopaedic brace or orthosis comprising first and second hinge plates which are relatively rotatable, the hinge comprising locking means which prevents further relative movement of the first and second plates when the plates reach a predetermined position wherein the locking means lies within the periphery of the plates.

Preferably, the locking means is in the form of a latch with a projection member, wherein the projection member is at right angles to the plane of the plates.

Preferably, the locking means has actuation means to selectively disengage the operation of the locking means.

The actuation means may be in the form of a cam lever which has an engaged position and a disengaged position, the cam lever permanently disengaging the projection when the disengaged position is selected.

Preferably, a biasing means is provided to bias the projection towards a position in which the locking means will lock when the plates are in the predetermined relative position.

The projection may be attached to a member which is pivotably connected to one of the first and second plates, with the axis of the pivot being parallel to the plane of the plate. Preferably, a hole is provided in the other of the first and second plates into which the projection is biased when the first and second plate hinge members reach the predetermined position.

The locking means has a lock actuator which is provided with an axle, a biasing leaf spring, a latching dog and a parking recess and a second element in the form of a cam lifter also having an axle together with a lifting cam and cam lifting levering.

The latching dog is an extension of the body of the lock actuator and is positively biased at right angles towards one of the hinge plates in the form of a locking plate by the leaf spring. When the hinge is rotated to the fully extended position, the locking dog, under the influence of the leaf spring, engages with stop-lock means in the form of latching hole situated at an appropriate position within the diameter of the circular end of the locking plate.

The lifting cam underlies that portion of the lock actuator which lies beyond the locking dog extension at the opposite end to its axle. The cam lifter is also provided, preferably integrally, with a cam lifting lever disposed at 45° to the lifting cam. The cam lifting lever portion extends through the a slot in the face of one of the hinge plates in the form of a circular recessed housing member to provide means for activating and de-activating the automatic hinge locking means.

From the "on" position, the cam lifting lever is moved from one side of its slot to the other which causes the cam to lift the dog out of engagement with the latching hole in the other of the hinge plates in the form of a locking plate, thereby releasing the hinge. Means are provided such that in this position the lifting cam is parked in the "off" position. The hinge may now move with free motion.

When the switch lever is moved back to the "on" position with the hinge flexed, the locking dog is brought into contact with the locking plate under the influence of the leaf spring. Under these circumstances, the hinge may move freely. However, when the position of full extension is reached, the dog engages hole, locking the hinge.

It is an important object of the present invention to provide a hinge structure which permits optional, automatic, locking at the fully extended position by means of a locking mechanism which operates by engaging a lock actuator mounted inside the limiting periphery of a latching plate provided. It is another object of the present invention to provide a hinge structure which permits optional, automatic, locking at the fully extended position by means of a locking mechanism which operates at right angles to the plane of the hinge arms.

Unlike prior art hinges, the hinge of the present invention uses an automatic locking mechanism wherein the latching dog operates at right angles to the locking plate and lies within the periphery thereof.

An embodiment of a hinge in accordance with the present invention is now described with reference to the accompanying drawings in which:

FIG. 5a and 5b are sections of the latching mechanism of the hinge of FIG. 1 showing the "free motion" and automatic extension locking positions.

Figure 1:
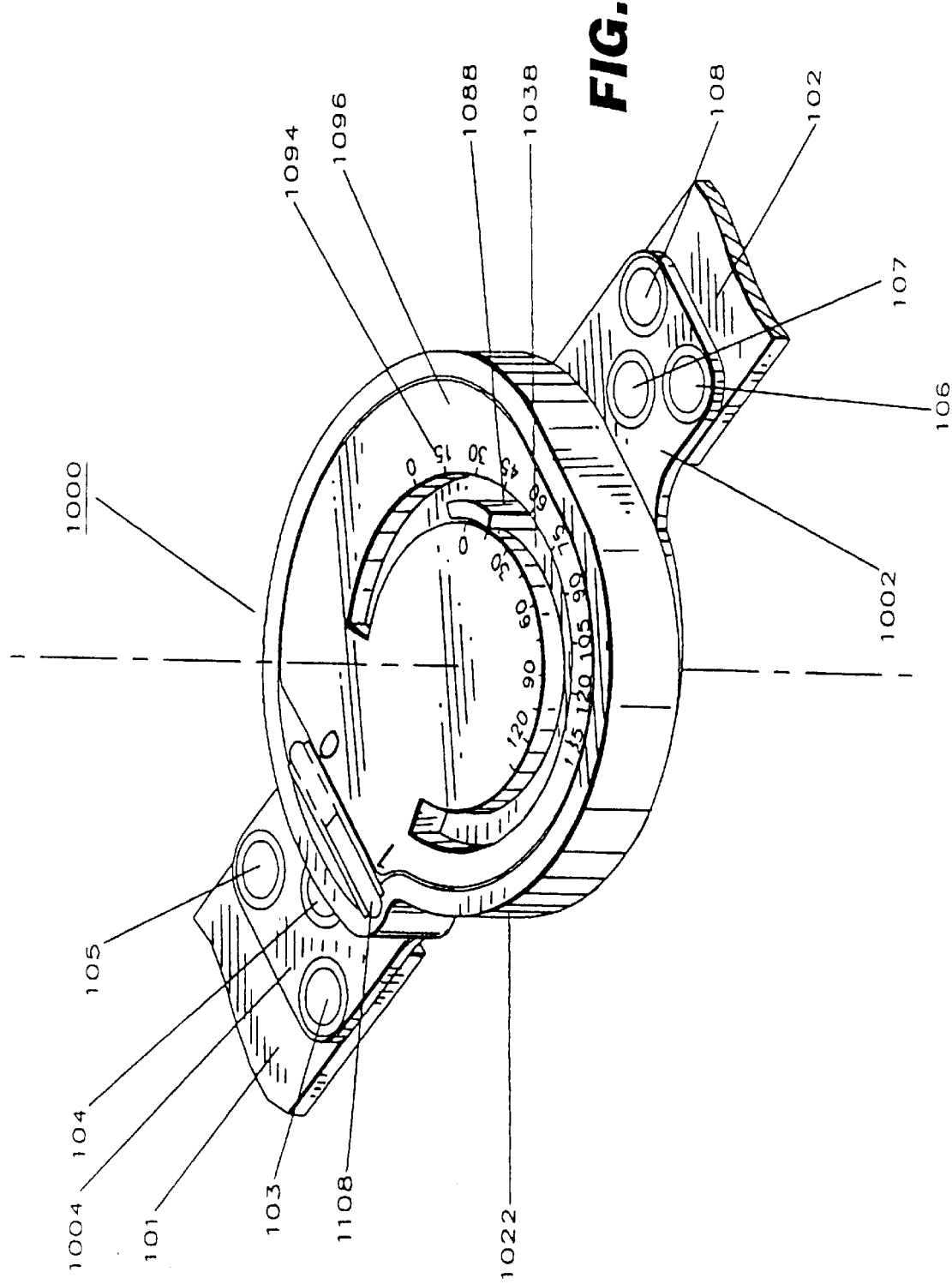
FIG. 1 is a diagrammatic perspective front view of a left hand hinge according to the present invention.
Figure 2:
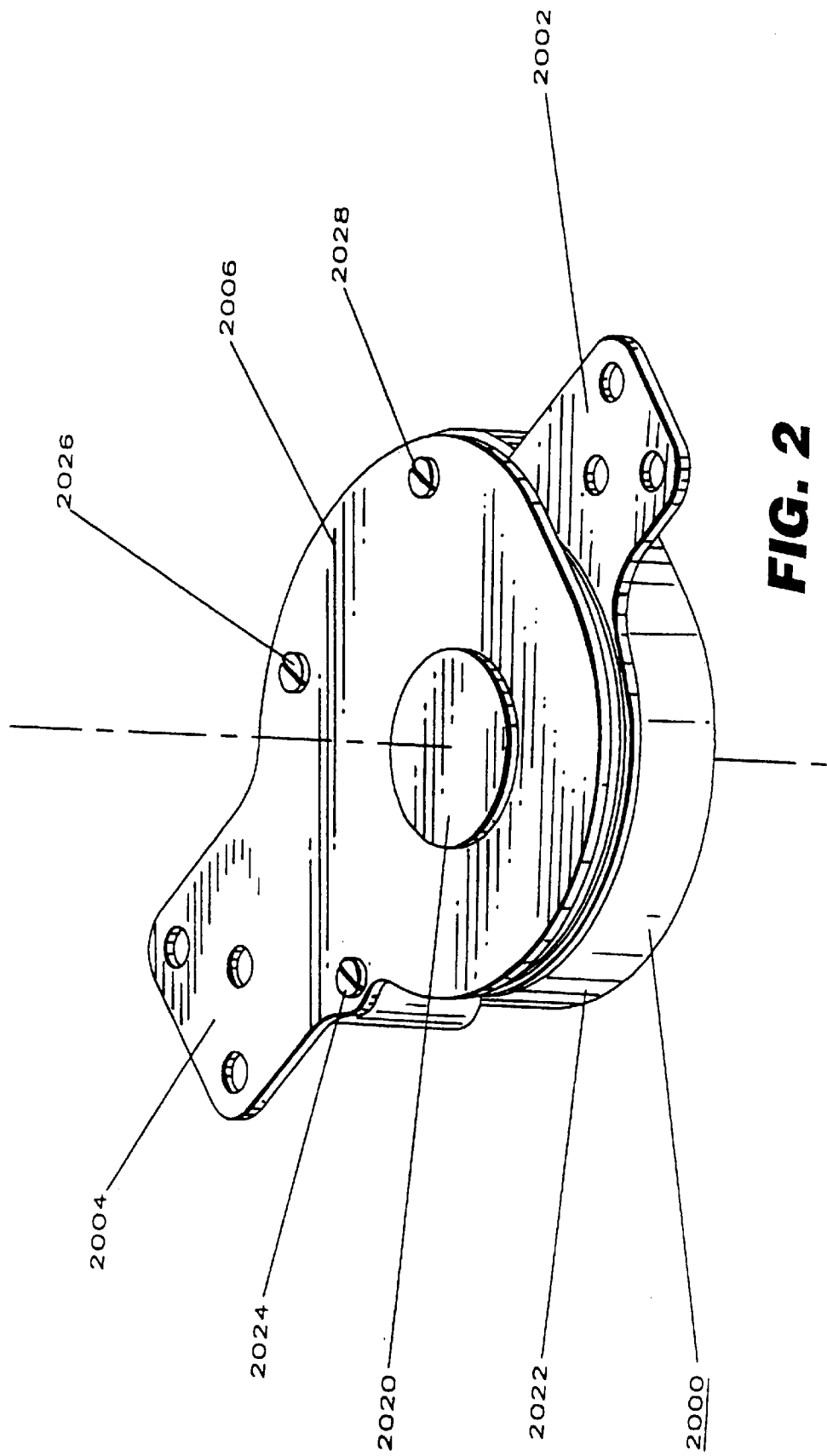
FIG. 2 is a diagrammatic perspective back view of a right hand hinge according to the present invention.

Referring first to FIG. 1, there is shown a diagrammatic, perspective, front view of a left hand single axis rotatable hinge 1000, according to the present invention, for use in an orthosis or orthopaedic brace 100. FIG. 2 shows a diagrammatic perspective back view of a right hand hinge 2000, the right hand hinge being substantially a mirror image of left hand hinge 1000. Brace arms 101 and 102 are secured to a left locking plate stub arm 1002 and left back plate stub arm 1004 by rivet means 103 to 108. This arrangement is preferred because it allows aluminium, which has the advantage of being light, to be used for generic brace arms which are generally quite large. In contradistinction back plates 1006 and 2006 and locking plates 1008 and 2008, according to the present invention are relatively small but are preferably made in stainless steel for strength and longevity.

Figure 3:
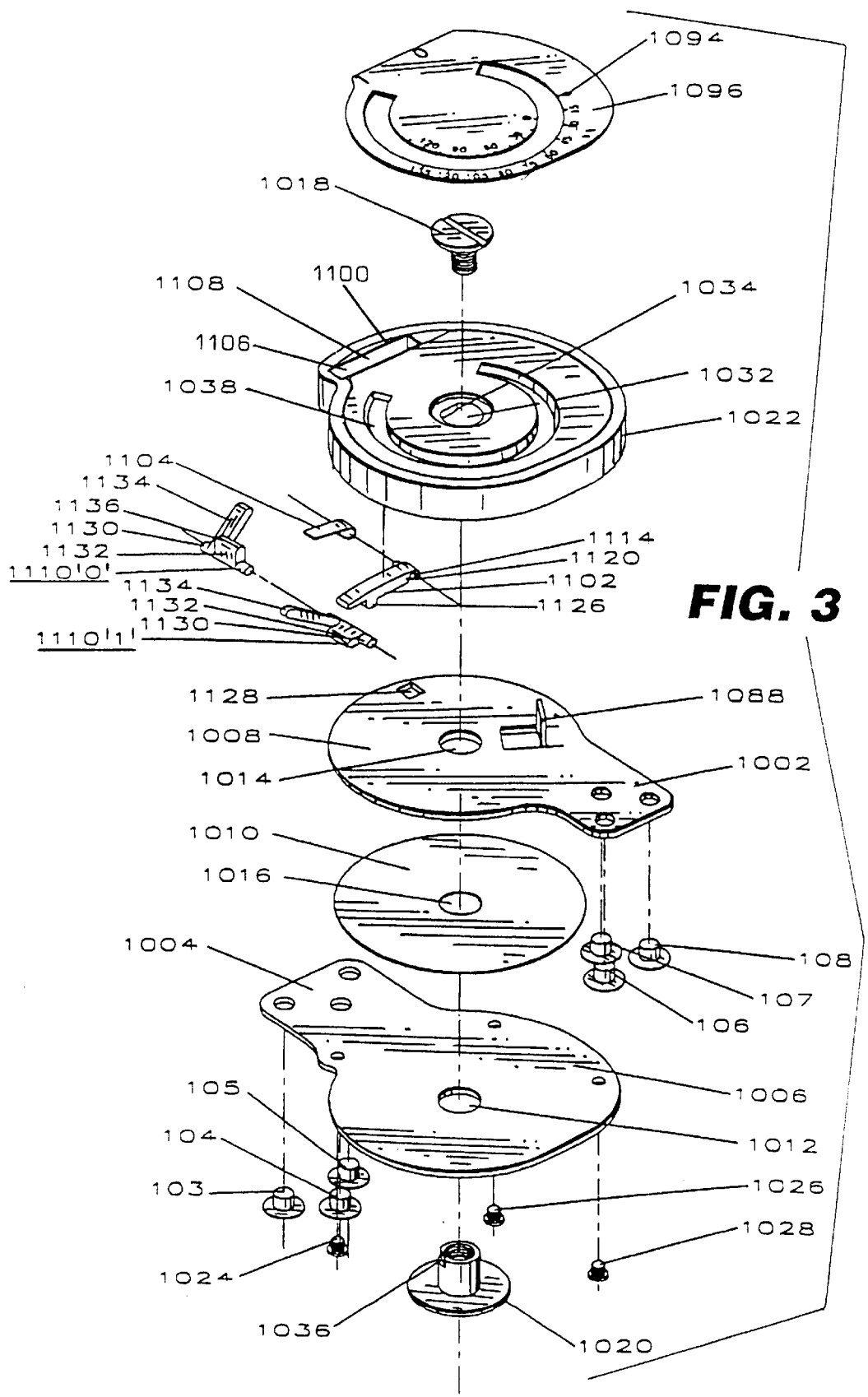
FIG. 3 is an exploded perspective view of the hinge of FIG. 1, showing the principal components.
Figure 4:
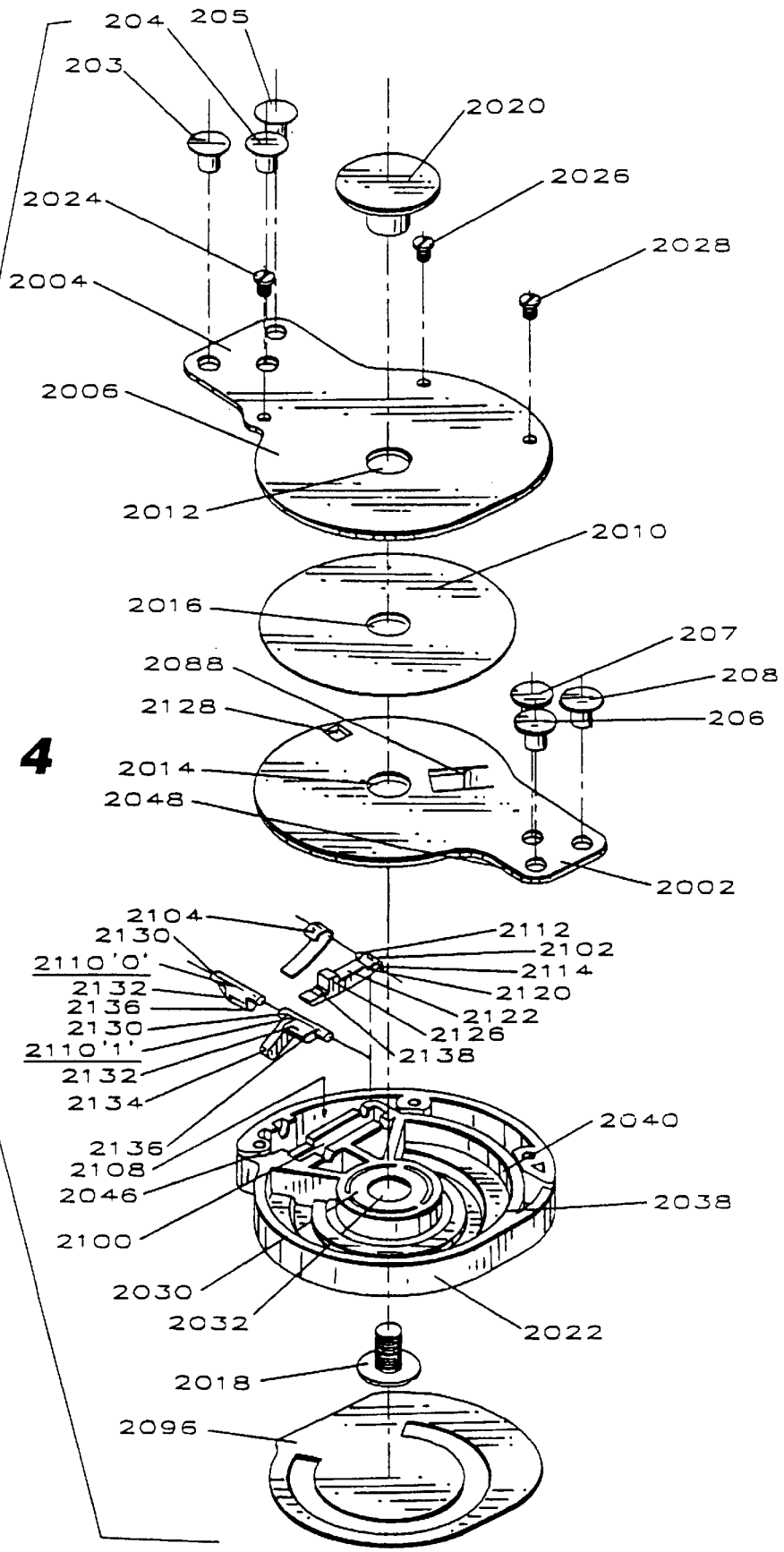
FIG. 4 is an exploded perspective view of the hinge of FIG. 2, showing the principal components.

As may best be seen with reference to FIGS. 3 and 4, back plates 1006 and 2006 and locking plates 1008 and 2008 are substantially circular, the diameters of the locking plates being slightly less than the principal diameter of the back plates which are extended and have a secondary, larger diameter. These elements are preferably manufactured commercially by pressing. Back plates 1006 and 2006 and locking plates 1008 and 2008 are spaced apart in a co-planar and concentric manner by circular plastic shims 1010 and 2010, which ensure smooth operation of the assembled hinges 1000 and 2000. Elements 1006; 2006, 1008; 2008 and 1010; 2010 are mutually adapted, by the provision of a central circular holes 1012; 2012, 1014; 2014 and 1016; 2016, respectively, of equal diameter, to receive slidingly, pivotal and securing means in the form of pivot bolts 1018; 2018 and blind flat headed nuts 1020; 2020.

Hinges 1000 and 2000 are each provided with a substantially circular recessed housings 1022 and 2022 respectively which is preferably moulded in high definition thermoplastics such as nylon 6 reinforced with 50% glass fibre for toughness. Alternatively, these components may be cast in a suitable aluminium alloy. The housings 1022 and 2022 are so sized that they fit over those parts of the peripheries of back plates 1006; 2006 which are not involved in flexion and extension motion and are each secured thereto by screw fixing means 1024, 1026, 1028 and 2024, 2026 and 2028. The housings 1022 and 2022 are each also adapted, by the provision of a central boss 1030; 2030, respectively having a through hole 1032; 2032, to receive pivot bolt 1018; 2018 and nut 1020; 2020.

Bosses 1030 and 2030 are each adapted by the provision of a flat 1034; 2034 to receive slidingly and non-rotatably, corresponding adaptations of part of each of the distal shanks of blind flat headed nuts 1020; 2020 in the form of flats 1036; 2036.

Circular recessed housings 1022 and 2022 may be with a concentric and arcuate through-slot, 1038; 2038, disposed inwardly from the periphery and extending over rather more than 270°.

A flange 1088; 2088 is provided, formed preferably by a three-sided broach through the locking plate 1008; 2008. The flange 1088; 2088 lies within the arcuate slot 1038; 2038 and limits the amount of movement of the hinge 1000; 2000.

Absolute hyperextension stop means are provided within moulded circular recessed housings 1022 and 2022 as indicated in FIG. 4 at 2046. This raised edge constitutes an abutment stop for edge 2048 of locking plate stub arm 2002.

Hinges 1000; 2000, according to the present invention are provided with an optionally activated, automatic locking means which, when activated, cause the hinge to lock in the fully extended position.

Lock actuator housings 1100; 2100, are each adapted to receive, slidingly and intimately, lock actuator 1102; 2102, each fitted with a biasing leaf spring 1104; 2104. Lock actuator housings 1100; 2100, are blind and substantially rectangular. Cam lifter housings 1106; 2106, each have substantially rectangular through-slots 1108; 2108, each adapted to receive, slidingly and rotatably, part of a cam lifter 1110; 2110. Lock actuator housings 1100; 2100, and cam lifter housings 1106; 2106, are disposed substantially at right angles to a radius of circular recessed housings 1022; 2022, in an essentially parallel relationship.

Figure 5B:
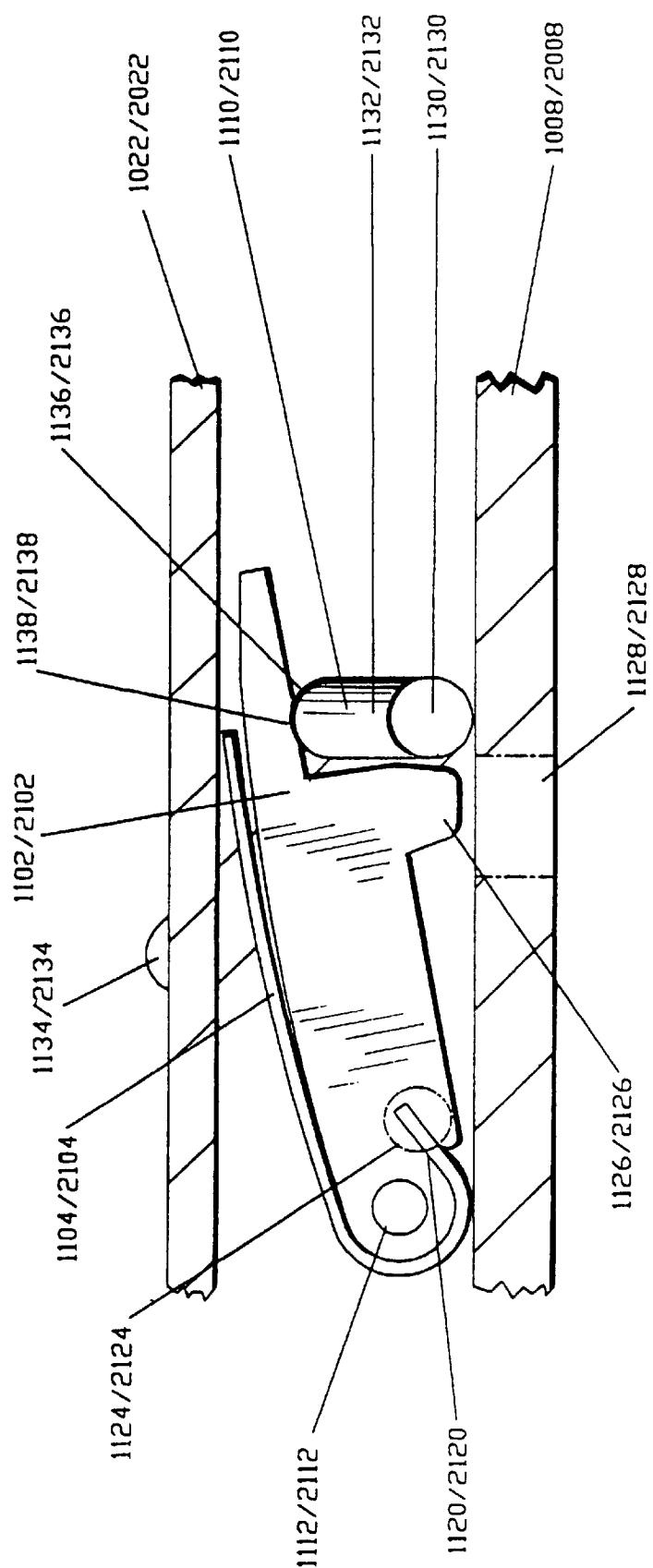

Lock actuators 1102; 2102, are small modified parallelepiped blocks, preferably made by investment casting in stainless steel, provided near a first end with stub axles 1112; 1114 and 2112; 2114, which locate in corresponding bearing recesses 1116; 1118 and 2116; 2118, in lock actuator housings 1100; 2100. Additionally, lock actuators 1102; 2102, are provided, in the same region, with slots 1120; 2120, in their undersides 1122; 2122, to receive, intimately, biasing leaf springs 1104; 2104, where they are secured in place by swaging, indicated in FIGS. 5a and 5b at 1124/2124. With continuing reference to these same figures there may be seen, near a second end, a latching dog 1126/2126, adapted to co-operate with latching holes 1128; 2128, in locking plates 1008 and 2008, respectively.

The lock actuators 1102; 2102 may be made of layers of metal plates adhered together.

Cam lifters 1110; 2110, are preferably made by investment casting in stainless steel and are each provided with an axle 1130; 2130, from which arises a short lifting cam 1132; 2132, respectively, having a thickness of the full diameter of axles 1130; 2130. Cam lifting levers 1134; 2134, are disposed at an angle of 45° to lifting cams 1132, 2132 and also preferably have a thickness of the full diameter of the axles 1130; 2130.

It will now be appreciated that it is cam lifting levers 1134; 1134, which are received into through slots 1108; 2108, in circular recessed housings 1022; 2022. By reference to FIG. 5a, it will be understood that, in the position illustrated, cam lifting levers 1134; 2134, rest at one end of through-slots 1108; 2108 and rounded ends 1136; 2136 of lifting cams 1132; 2132, engage with matching rounded recesses 1138/2138, in the underside of lock actuators 1116/2116.

It will further be appreciated that rounded recesses 1138/2138, are so arranged that with cam lifting levers 1134; 2134, in the position shown, the locking mechanism is "parked" in a stable but readily disengageable manner with lifting cams 1132; 2132, vertical at top dead centre. In this position, indicated on the markings label with the binary symbol "0" to indicate that the locking mechanism is inactive, biasing leaf spring 1104; 2104 is under near-maximum compression but is not able to drive latching dog 1126; 2126 against locking plate 1108; 2108. However, a small amount of bias is applied to rounded recesses 1138/2138 in co-operation with rounded ends 1136; 2136 of lifting cams 1132; 2132, imparting both stability to the parking arrangement and a smooth but positive feel to the mechanism as it is switched into or out of the parked position.

When cam lifting levers 1134; 2134 are moved to the opposite end of through-slots 1108; 2108, preferably indicated on the markings label with the binary symbol "1" to indicate that the locking mechanism is active, lifting cams 1132; 2132, disengage from matching rounded recesses 1138/2138 and move through 90°, coming to rest in the horizontal position and parallel to the undersides 1122; 2122, of lock actuators 1102; 2102.

It is to be understood that the length of lifting cams 1132; 2132, is so arranged in relation to the diameter of axles 1112; 1114 and 2112; 2114 and the vertical dimension and travel of latching dogs 1126/2126, that in the parked or "off" position, the latter cannot contact locking plate 1008; 2008 nor engage with latching holes 1128; 2128 therein.

It is further to be understood that these dimensions are also arranged in conjunction with that of the thickness of locking plate 1008; 2008, such that in the active, engaged or on position, latching dogs 1126/2126, can just fully engage with latching holes 1128; 2128. In the active position, latching dogs 1126/2126 are always driven against locking plates 1008; 2008 under the influence of biasing leaf springs 1104; 2104, whatever the flexion angle of hinges 1000; 2000. However, as hinges 1000; 2000 are moved close to the fully extended position, latching dogs 1126/2126, arrive at the leading margins of latching holes 1128; 2128, respectively, with which they engage under the biasing action of biasing leaf springs 1104; 2104. It will be appreciated that the dimension of circular recessed housings 1022; 2022 and cam lifting levers 1134; 2134 are selected to ensure that the latter may be readily operated so as to disengage latching dogs 1126/2126 from latching holes 1128; 2128, even when the user is moderately flexion loading the hinges.

At this point the motion options of the instant hinge and locking mechanisms may be summarised. Starting in the on position, with the latching dog engaged with the latching hole in the backplate, the cam lifting lever is manually moved through about 60° to lift the latching dog out of engagement. In fact, the profiles of the rounded end of the lifting cam, the co-operating rounded recess the lock actuator, and a biasing spring selected for appropriate duty and duty power are so arranged that once the latching dog is disengaged, the cam lifting lever will tend to move through the remainder of its intended 90° travel without further applied force. In this position the cam profiles are in mutual contact in such a manner as to "park" the switch lever in the "off" position. In the "off" position, the hinge may move with free motion.

When the cam lifting lever is moved back to the "on" position with the hinge flexed, the latching dog is brought into with the locking plate under the influence of the leaf spring. Under these circumstances, the hinge may move freely within the limits set with its range of motion control system. However, if the range of motion system is set so as to allow full extension, when that position is reached, the latching dog once again engages the latching hole, locking the hinge in the fully extended position.

In conventional detent locking mechanisms of the prior art, a dogging element engages, in the same plane, with a receiving element in the edge of a locking plate. In such an arrangement, the dogging element, together with any biasing element, must necessarily lie outside the periphery of the receiving element.

In further marked contradistinction, the present invention provides for a latching mechanism where the dogging element together with a biasing element is at right angles to the receiving element and is further mounted within the periphery of the receiving element. By these novel means, hinges according to the present invention may be made substantially more compactly and neatly than prior art hinges.

The instant invention employs only a small number of parts and is, therefore, generally simpler and easier to construct and more economical to supply than prior art range of motion hinges. Additionally, the instant hinge offers incremental adjustment at smaller incremental angles than are generally available with prior art incremental range of motion hinges. Furthermore, adjustments to the extension and flexion stops of the instant hinge may be made more rapidly and easily than with previous hinges and no special tools are required.

The preferred embodiment of the present invention immediately hereinbefore described is given by way of example and it will be clear to those skilled in the art that numerous other variations may be derived from this disclosure without departing from the scope, intent and spirit of the novelty thereof.

I claim:

1. A hinge for use in an orthopaedic brace or orthosis comprising first and second hinge plates which are relatively rotatable, the hinge comprising locking means which prevents further relative movements of the first and second plates when the plates reach a predetermined position, said locking means is in the form of a latch with a projection member which is at right angles to the plane of the plates and a hole is provided in one of the first or second plates to receive said projection member thereby locking the hinge from further rotation, and wherein the locking means lies within the periphery of the plates.

2. A hinge as claimed in claim 1, wherein the locking means has actuation means to selectively disengage the operation of the locking means.

3. A hinge as claimed in claimed in claim 2, wherein the actuation means is in the form of a cam lever which has an engaged position and a disengaged position, the cam lever permanently disengaging the projection when the disengaged position is selected.

4. A hinge as claimed in claim 1, wherein a biasing means is provided to bias the projection member towards a position in which the locking means will lock when the plates are in the predetermined relative position.

5. A hinge as claimed in claim 1, wherein the projection member is attached to a member which is pivotably connected to one of the first and second plates, with the axis of the pivot being parallel to the plane of the plate.

* * * * *